(12) United States Patent
Franjic et al.

(10) Patent No.: US 10,575,921 B2
(45) Date of Patent: Mar. 3, 2020

(54) CAMERA SYSTEM FOR PROVIDING IMAGES WITH SIMULTANEOUS HIGH RESOLUTION AND LARGE DEPTH OF FIELD

(71) Applicant: SYNAPTIVE MEDICAL (BARBADOS) INC., Bridgetown (BB)

(72) Inventors: Kresimir Franjic, Toronto (CA); Kai Hynna, Toronto (CA); Yanhui Bai, Toronto (CA); Michael Frank Gunter Wood, Toronto (CA); Michael Peter Bulk, Toronto (CA); Tammy Kee-Wai Lee, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/558,641

(22) PCT Filed: Dec. 1, 2016

(86) PCT No.: PCT/IB2016/057276
§ 371 (c)(1),
(2) Date: Sep. 15, 2017

(87) PCT Pub. No.: WO2018/100414
PCT Pub. Date: Jun. 7, 2008

(65) Prior Publication Data
US 2018/0243045 A1 Aug. 30, 2018

(51) Int. Cl.
*A61B 90/00* (2016.01)
*A61B 34/20* (2016.01)
(Continued)

(52) U.S. Cl.
CPC ............ *A61B 90/361* (2016.02); *A61B 34/20* (2016.02); *A61B 90/30* (2016.02); *G03B 7/00* (2013.01);
(Continued)

(58) Field of Classification Search
CPC ....... A61B 90/361; A61B 34/20; A61B 90/20; G06T 7/55; G03B 7/00; G03B 9/04; H04N 5/23212; H04N 5/23229
See application file for complete search history.

(56) References Cited

U.S. PATENT DOCUMENTS 5,748,371 A    5/1998   Cathey, Jr. et al.
8,937,651 B2 * 1/2015   Guissin .................. G02B 13/06
                                                    348/239
(Continued)

FOREIGN PATENT DOCUMENTS

EP      2096483 A1    9/2009
WO   2016/142738 A1    9/2016

OTHER PUBLICATIONS

International Search Report dated Nov. 24, 2015 for International Application No. PCT/IB2015/051704.
(Continued)

*Primary Examiner* — Maria E Vazquez Colon
(74) *Attorney, Agent, or Firm* — Perry + Currier, Inc.

(57) ABSTRACT

A camera system for providing images with simultaneous high resolution and large depth of field is provided. The system includes: a camera device having a field of view, the camera device configured to automatically acquire: a first image of the field of view at a first numerical aperture; and a second image of the field of view at a second numerical aperture smaller than the first numerical aperture; an image processing unit configured to combine the first image with the second image into a single image by: extracting a
(Continued)

higher-resolution in-focus portion of the first image; and replacing a corresponding lower-resolution portion of the second image with the higher-resolution in-focus portion of the first image; and, a display device in communication with the image processing unit, the display device configured to render the single image.

11 Claims, 14 Drawing Sheets

(51) Int. Cl.
G03B 9/04 (2006.01)
G03B 7/00 (2014.01)
A61B 90/30 (2016.01)
G06T 7/55 (2017.01)
H04N 5/232 (2006.01)

(52) U.S. Cl.
CPC ............... *G03B 9/04* (2013.01); *G06T 7/55* (2017.01); *H04N 5/23212* (2013.01); *H04N 5/23229* (2013.01); *A61B 2034/2055* (2016.02)

(56) References Cited

U.S. PATENT DOCUMENTS

| | | | | |
|---|---|---|---|---|
| 9,684,841 | B2* | 6/2017 | Cheung | G06T 5/50 |
| 2001/0012053 | A1 | 8/2001 | Nakamura | |
| 2002/0181950 | A1* | 12/2002 | Kamata | C23C 16/455 396/170 |
| 2005/0140820 | A1 | 6/2005 | Takeuchi et al. | |
| 2007/0016009 | A1* | 1/2007 | Lakin | A61B 90/39 600/424 |
| 2008/0151041 | A1 | 6/2008 | Shafer | |
| 2009/0015689 | A1 | 1/2009 | Murayama | |
| 2009/0303375 | A1* | 12/2009 | Ohyama | H04N 5/23219 348/333.12 |
| 2011/0141239 | A1 | 6/2011 | Kennedy | |
| 2011/0310218 | A1* | 12/2011 | Harding | G02B 15/02 348/36 |
| 2013/0046137 | A1 | 2/2013 | Zhao et al. | |
| 2013/0338439 | A1 | 12/2013 | Kosugi et al. | |
| 2014/0085398 | A1 | 3/2014 | Tian et al. | |
| 2015/0346583 | A1 | 12/2015 | Yoshizawa et al. | |

OTHER PUBLICATIONS

Written Opinion dated Nov. 24, 2015 for International Application No. PCT/IB2015/051704.
Examination Report dated Sep. 12, 2017, by CIPO, re Canadian Patent Application No. 2977172.
Grewe. Jul. 1, 2011. Fast two-layer two-photon imaging of neuronal cell populations using an electrically tunable lens. Biomedical Optics Express. vol. 2 (7). pp. 2035-2046.
Zuo. Oct. 7, 1013. High-speed transport-ofOintensity phase microscopy with an electrically tunable lens. Optics Express. vol. 21 (20). pp. 24060-24075.
USPTO, Notice of Allowance and Fee(s) Due, dated Apr. 4, 2018, re U.S. Appl. No. 15/549,804.
International Search Report dated Aug. 18, 2017, by ISA, re PCT Patent Application No. PCT/IB2016/057276.
Written Opinion dated Aug. 18, 2017, by ISA, re PCT Patent Application No. PCT/IB2016/057276.
USPTO, Notice of Allowance and Fee(s) Due, dated Apr. 12, 2019, re U.S. Appl. No. 16/026,678.
Alex Paul, "A new sense for depth of field." IEEE transactions on pattern analysis and machine intelligence 4 (1987): 523-531.
Klaus-Peter Zimmer, "Advances in Stereomicroscopy". Optical Design and Engineering III. vol. 7100. International Society for Optics and Photonics. 2008.
Ricoh, "Extended Depth-of-Field Camera". Ricoh.Imagine.Change, Dec. 3, 2013, http://www.ricoh.comiabout/ ;ompanyitechnologyttech/050_edof html. (available at: https://web.archive.orgiweb/20140803204423/http://www.ricoh.com/about/company/technology/tech/050_edpf.html).
Raytrix GmbH. "3D Light Field Camera Technology." Raytrix, Mar. 9, 2015, http://www.raytrix.de/index.php/Cameras.html. (Available at: https://web.archive.org/web/20150321070847/http://www.raytrix.de/index.php/Cameras.html).
Häusler, Gerd. "A method to increase the depth of focus by two step image processing." Optics Communications 6.1 (1972): 38-42.
Bhardwaj, Adit, and Shanmuganathan, Raman. "PCA-HDR: A robust PCA based solution to HDR imaging." 2014 International Conference on Signal Processing and Communications (SPCOM). IEEE, 2014.
USPTO, Non-Final Rejection, dated Sep. 3, 2019, re U.S. Appl. No. 16/026,678.

* cited by examiner

CAMERA SYSTEM FOR PROVIDING IMAGES WITH SIMULTANEOUS HIGH RESOLUTION AND LARGE DEPTH OF FIELD

This application is a 371 of PCT International Application number PCT/IB2016/057276 filed Dec. 1, 2016, the entire contents of which are hereby incorporated by reference.

FIELD

The specification relates generally to camera systems, and specifically a camera system for providing images with simultaneous high resolution and large depth of field, which can be used for minimally invasive surgery and/or therapy, and image guided medical procedures.

BACKGROUND

When observing an object under a microscope, it is often preferable to have simultaneous high image resolution together with a large depth of field. An example is a surgical microscope where surgeons need sharp resolution of an affected tissue point image but also need a large depth of field to provide orientation and context. However, for a fixed optical system these parameters are not independent and are fundamentally related through the numerical aperture (NA) of the optical system. For example, approximate formulas for each of depth of field (DOF) and a smallest feature that can be resolved (RES) for an optical system are: $DOF=\lambda/NA^2$; and $RES=0.61\ \lambda/NA$ (where $\lambda$ is the average wavelength of illumination light, RES indicates a smallest feature that can be resolved. Hence as NA decreases in order to increase a resolution of an optical system (e.g. decrease the RES value), the DOF increases. Hence it is clear that increasing resolution is achieved at the expense of decreasing depth of field, and vice versa. In particular, since DOF depends inversely on square of NA, an increase in resolution (e.g. a decrease in RES) is very taxing on the DOF.

In conventional optical systems, the NA of a microscope typically retains the same size during a single image or video acquisition which means that a decision about the trade-off between high resolution (e.g. reducing RES) and large depth of field (e.g. increase DOF) has to be made before each image or video sequence acquisition. It is possible to acquire an image/video with high resolution with small depth of field or vice versa but not is not possible to achieve both simultaneously.

SUMMARY

The present disclosure is generally directed to image guided medical procedures using an access port and/or open surgery. The port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Further, a camera system is provided that includes a camera device compatible with surgical access ports and/or open surgery, the camera device having a field of view, the camera device configured to automatically acquire: a first image of the field of view at a first numerical aperture; and a second image of the field of view at a second numerical aperture smaller than the first numerical aperture. Hence, the first image has a smaller depth of field and a higher resolution than the second image. The images can be combined by extracting a higher-resolution in-focus portion of the first image and replacing a corresponding lower-resolution portion of the second image with the higher-resolution in-focus portion of the first image. Hence, a surgeon can view the resulting combined single image that includes the higher-resolution in-focus portion of the first image, which can be tissue of interest on which surgery is to occur, with a lower-resolution in-focus background region of the second image. Various devices can be used to provide the varying numerical apertures, each including a dynamic iris that can change an aperture sized. In some of these devices, plate with at least two fixed size apertures are used, and an actuator moves the apertures in and out of a light path. In other devices, the dynamic iris can be varied continuously for example using a display device and/or a mechanical iris.

An aspect of the specification provides a camera system comprising: a camera device having a field of view, the camera device configured to automatically acquire: a first image of the field of view at a first numerical aperture; and a second image of the field of view at a second numerical aperture smaller than the first numerical aperture; an image processing unit configured to combine the first image with the second image into a single image by: extracting a higher-resolution in-focus portion of the first image; and replacing a corresponding lower-resolution portion of the second image with the higher-resolution in-focus portion of the first image; and, a display device in communication with the image processing unit, the display device configured to render the single image.

The camera device can comprise: a plate including a first aperture, defining the first numerical aperture, and a second aperture, defining the second numerical aperture, a diameter of the first aperture being larger than a respective diameter of the second aperture; and an actuator configured to automatically move the plate relative to the field of view of the camera device such that the first image is automatically acquired using the first aperture and the second image is automatically acquired using the second aperture.

The camera device can comprise: a transmissive display device configured to form a first light aperture, defining the first numerical aperture, and a second light aperture, defining the second numerical aperture, a diameter of the first light aperture being larger than a respective diameter of the second light aperture; and controller configured to automatically switch the transmissive display device between the first light aperture and the second light aperture, such that the first image is automatically acquired using the first light aperture and the second image is automatically acquired using the second light aperture.

The camera device can comprise: a first sensor system having a first aperture defining the first numerical aperture; a second sensor system having a second aperture defining the second numerical aperture; and a beam splitter configured to split light from the field of view between the first sensor system and the second sensor system.

The camera device can comprise a dynamic iris configured to switch between the first numerical aperture and the second numerical aperture.

The camera device can be configured to switch between the first numerical aperture and the second numerical aperture at a given rate, such that the first image and the second image are acquired at a rate half of the given rate, and the single image is generated at half the given rate. The given rate can be at least 60 Hz.

The image processing unit can be further configured to determine the higher-resolution in-focus portion of the first image using one or more contrast analysis algorithms.

The camera system can further comprise a tracking device configured to be tracked by a navigation system.

A further aspect of the specification provides a method comprising: at a system comprising: a camera device having a field of view and configured to change between at least two numerical apertures, an image processing device; and a display device in communication with the image processing unit, acquiring, using the camera device, a first image of the field of view at a first numerical aperture; acquiring, using the camera device, a second image of the field of view at a second numerical aperture smaller than the first numerical aperture; combining, using the image processing unit, the first image with the second image into a single image by: extracting a higher-resolution in-focus portion of the first image; and replacing a corresponding lower-resolution portion of the second image with the higher-resolution in-focus portion of the first image; and, rendering, at the display device, the single image.

The camera device can comprise a plate including a first aperture, defining the first numerical aperture, and a second aperture, defining the second numerical aperture, a diameter of the first aperture being larger than a respective diameter of the second aperture; and an actuator configured to automatically move the plate relative to the field of view of the camera device such that the first image is automatically acquired using the first aperture and the second image is automatically acquired using the second aperture.

The camera device can comprise: a transmissive display device configured to form a first light aperture, defining the first numerical aperture, and a second light aperture, defining the second numerical aperture, a diameter of the first light aperture being larger than a respective diameter of the second light aperture; and controller configured to automatically switch the transmissive display device between the first light aperture and the second light aperture, such that the first image is automatically acquired using the first light aperture and the second image is automatically acquired using the second light aperture.

The camera device can comprise: a first sensor system having a first aperture defining the first numerical aperture; a second sensor system having a second aperture defining the second numerical aperture; and a beam splitter configured to split light from the field of view between the first sensor system and the second sensor system.

The camera device can comprise a dynamic iris configured to switch between the first numerical aperture and the second numerical aperture.

The camera device can be configured to switch between the first numerical aperture and the second numerical aperture at a given rate, such that the first image and the second image are acquired at a rate half of the given rate, and the single image is generated at half the given rate. The given rate can be at least 60 Hz.

The method can further comprise: determining the higher-resolution in-focus portion of the first image using one or more contrast analysis algorithms.

The system can further comprise a tracking device configured to be tracked by a navigation system.

A further aspect of the specification provides a computer-readable medium storing a computer program, wherein execution of the computer program is for: at a system comprising: a camera device having a field of view and configured to change between at least two numerical apertures, an image processing device; and a display device in communication with the image processing unit, acquiring, using the camera device, a first image of the field of view at a first numerical aperture; acquiring, using the camera device, a second image of the field of view at a second numerical aperture smaller than the first numerical aperture; combining, using the image processing unit, the first image with the second image into a single image by: extracting a higher-resolution in-focus portion of the first image; and replacing a corresponding lower-resolution portion of the second image with the higher-resolution in-focus portion of the first image; and, rendering, at the display device, the single image. The computer-readable medium can comprise non-transitory computer-readable medium.

BRIEF DESCRIPTIONS OF THE DRAWINGS

For a better understanding of the various implementations described herein and to show more clearly how they may be carried into effect, reference will now be made, by way of example only, to the accompanying drawings in which.

Figure 8:
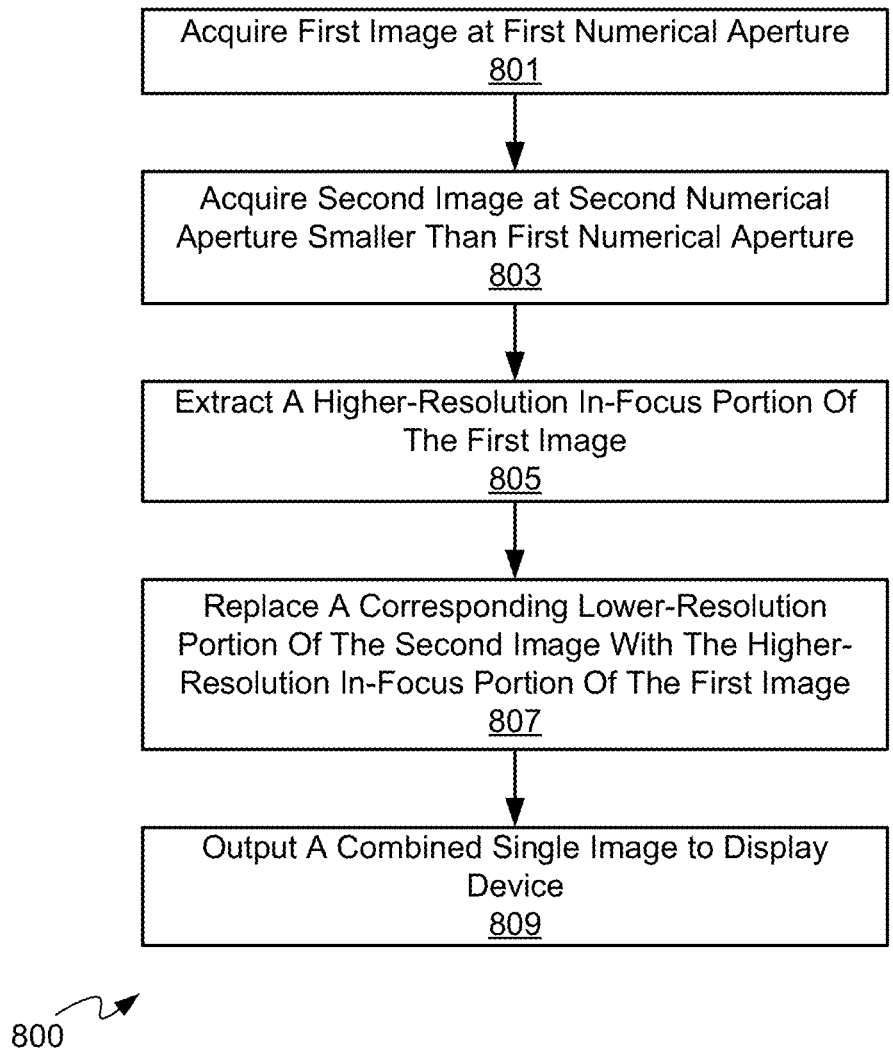

FIG. 8 a block diagram of a method for to acquire and combine images at different numerical apertures, according to non-limiting implementations.

Figure 9:
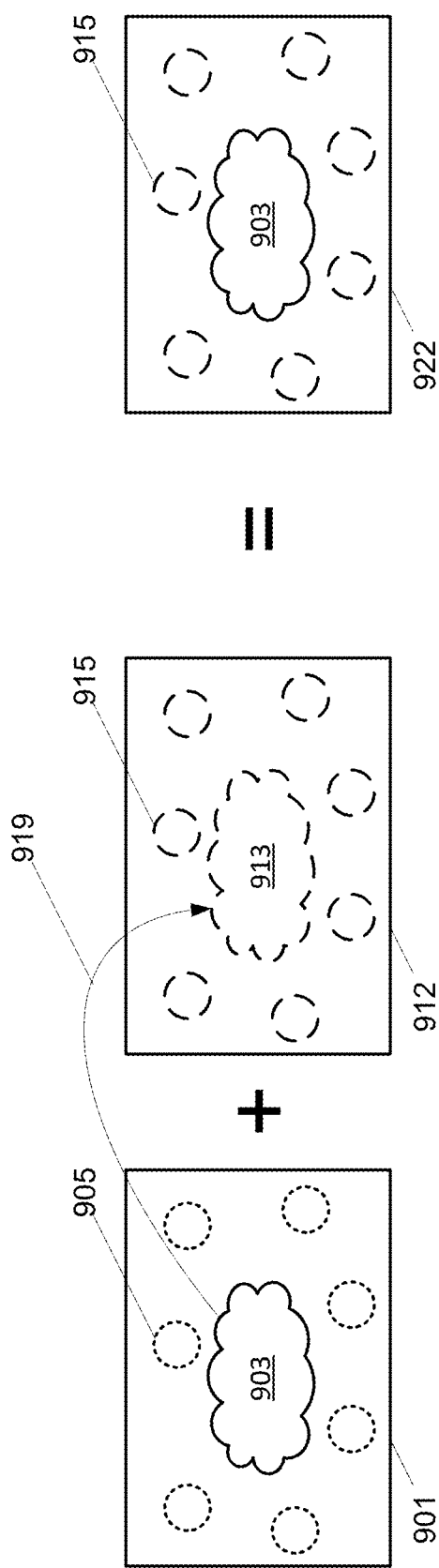

FIG. 9 depicts an example of the method of FIG. 8, according to non-limiting implementations.

Figure 6:
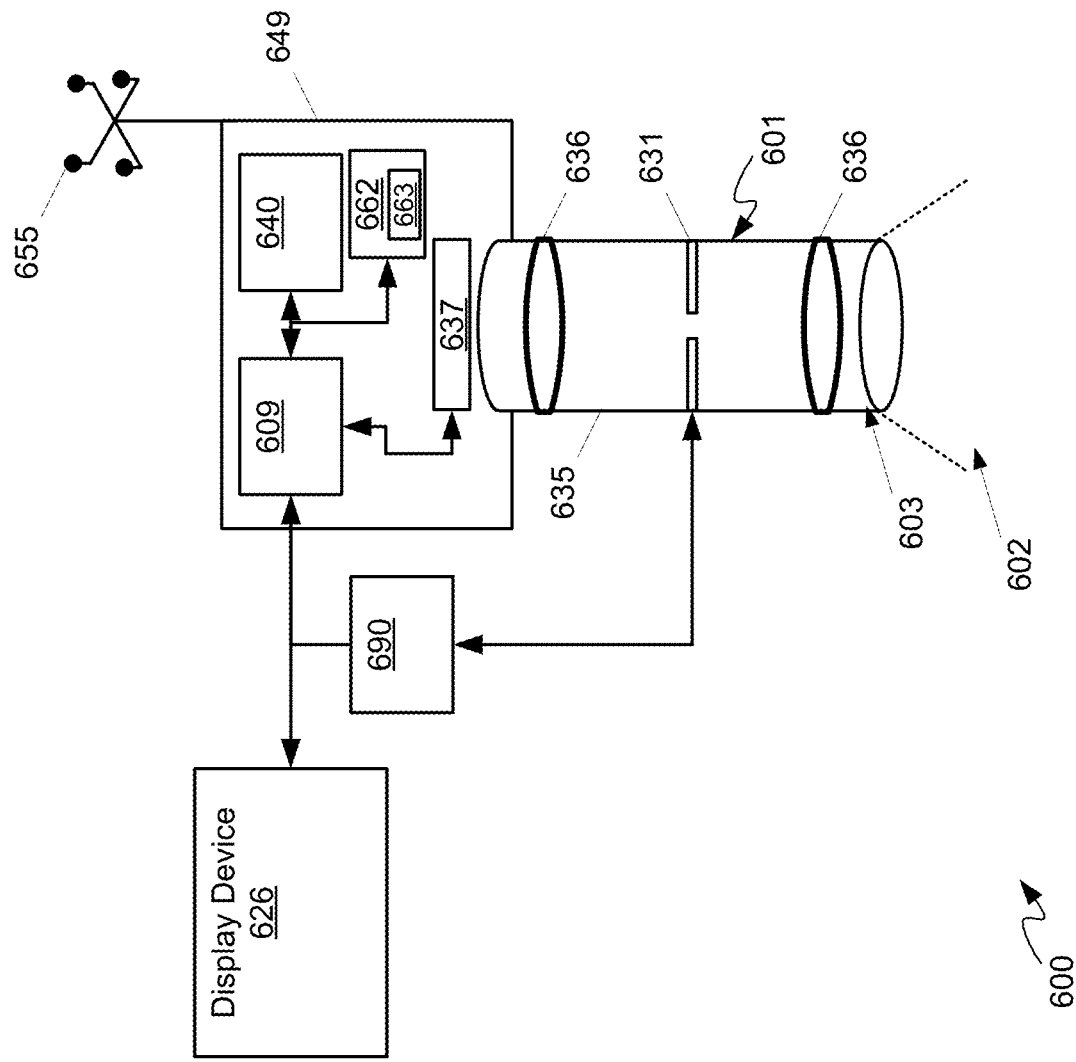
FIG. 6 depicts a schematic diagram of a camera system with automatic alternation between two numerical apertures, according to non-limiting implementations.
Figure 10:
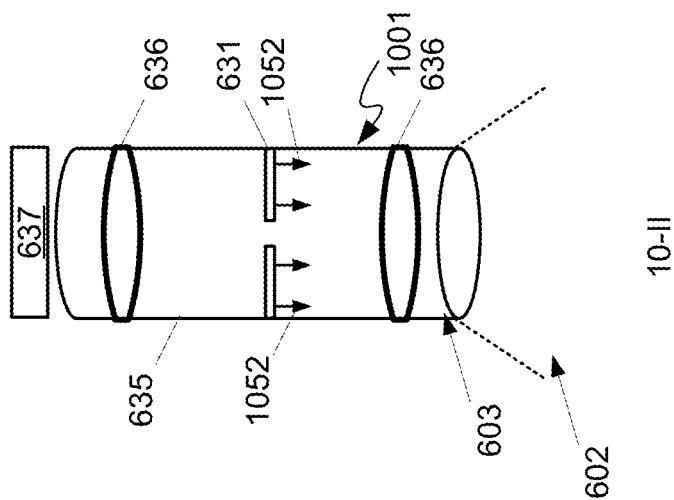
Figure 10:
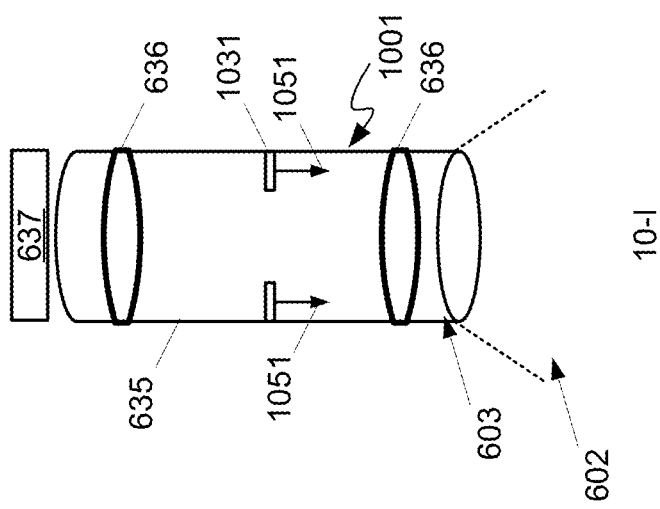

FIG. 10 a camera device that can be used with the system of FIG. 6, and that includes a light emitting dynamic iris, with the light emitting dynamic iris in two configurations, according to non-limiting implementations.

Figure 11:
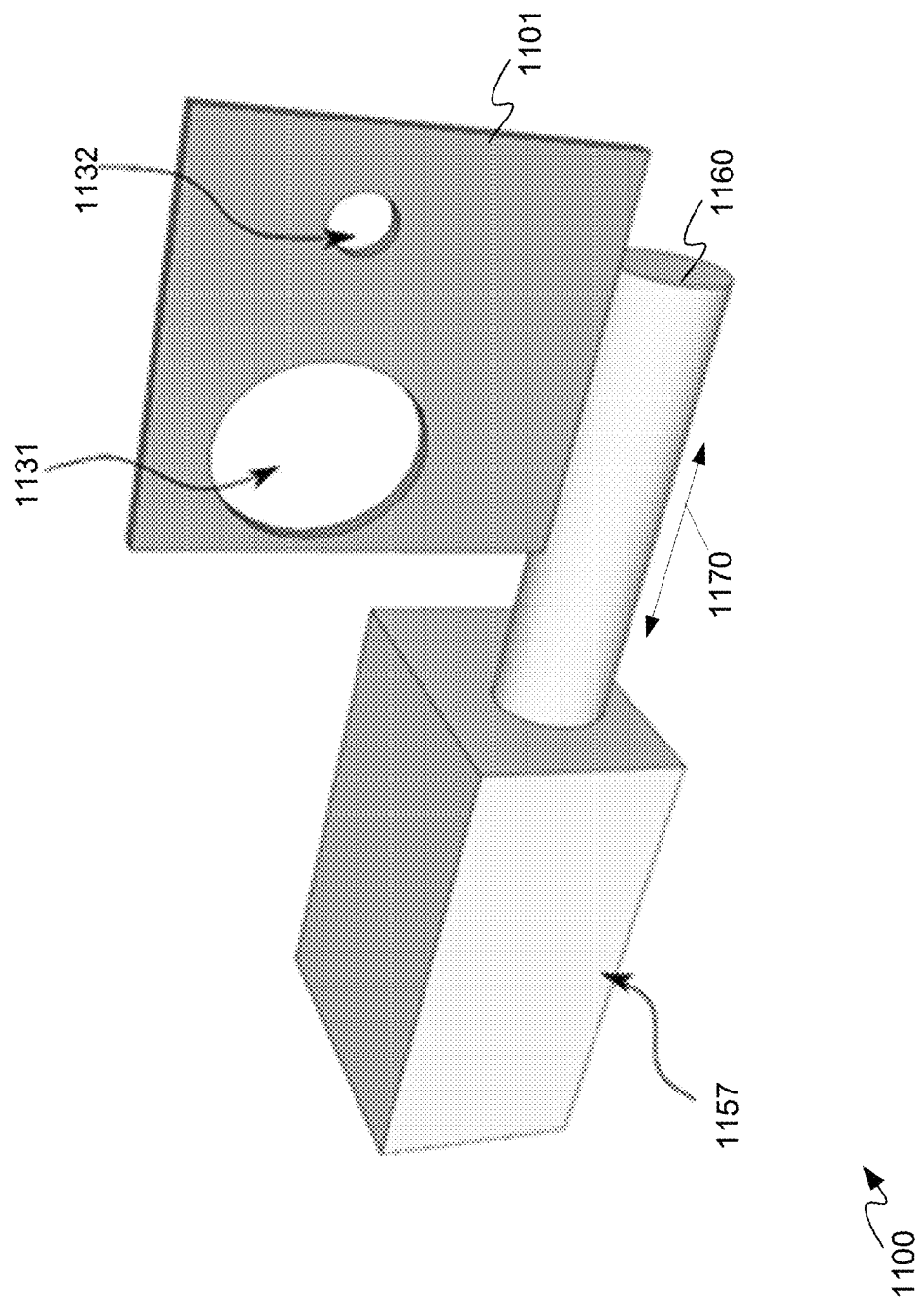

FIG. 11 depicts a dynamic iris device that can be used with the system of FIG. 6, according to non-limiting implementations.

Figure 12:
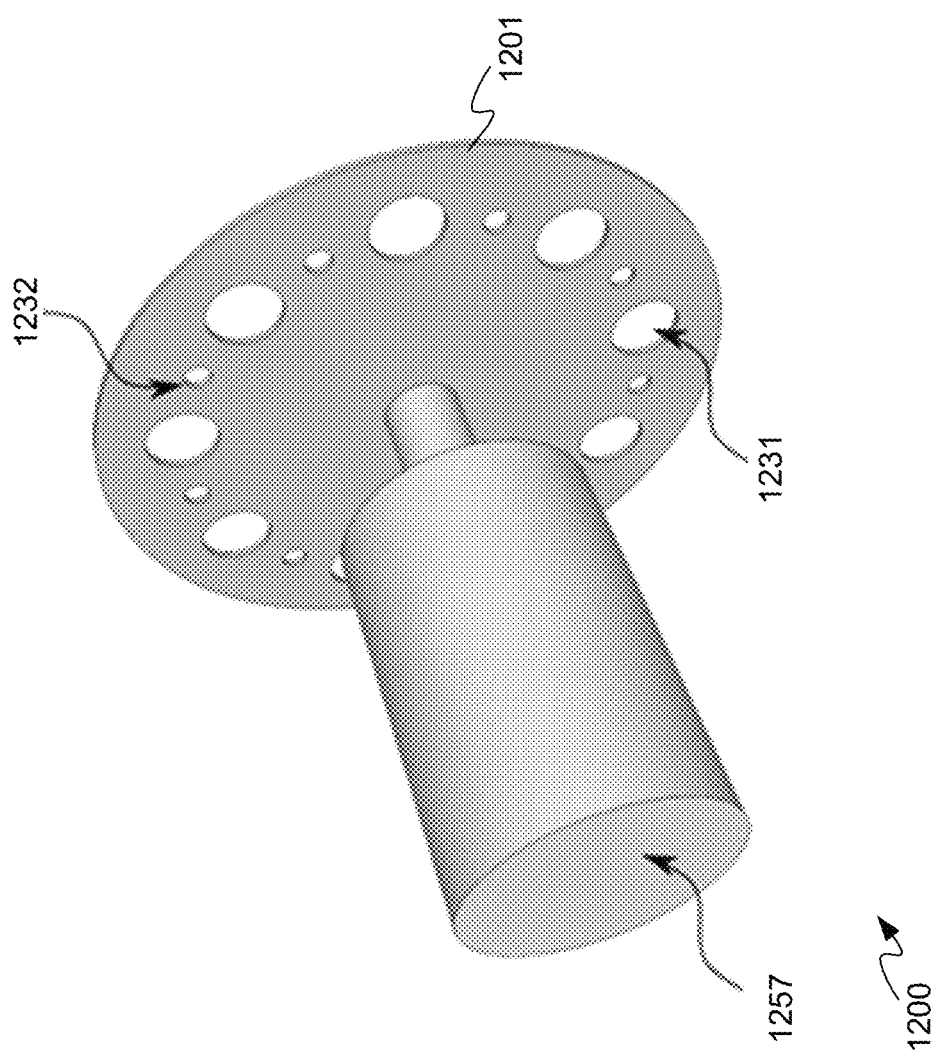

FIG. 12 depicts another dynamic iris device that can be used with the system of FIG. 6, according to non-limiting implementations.

Figure 13:
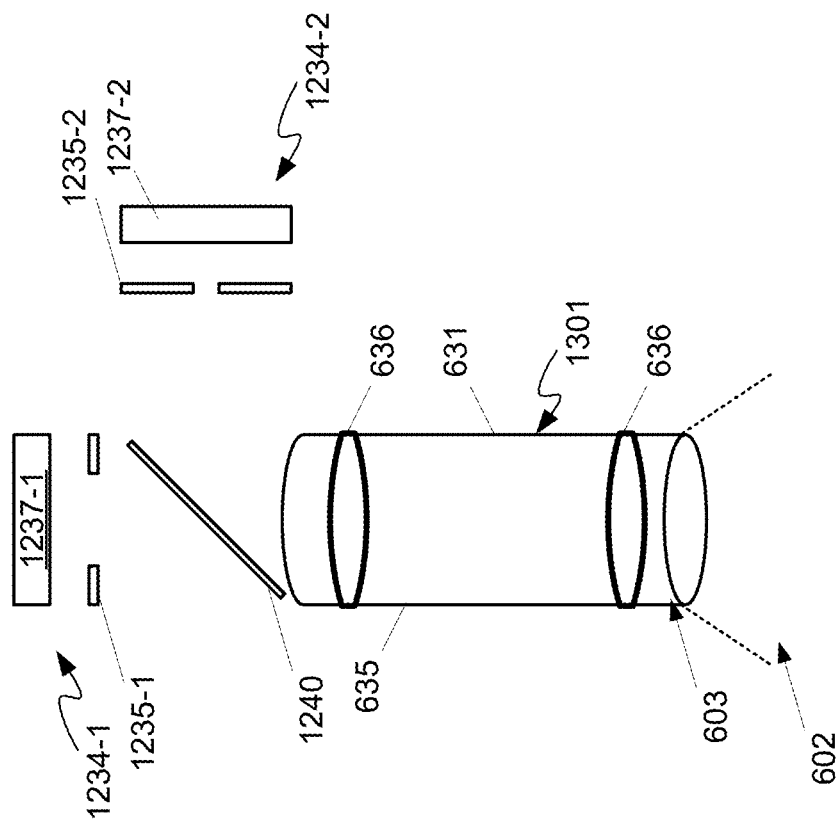

FIG. 13 depicts a camera device having two sensor systems that can be used with the system of FIG. 6, according to non-limiting implementations.

Figure 14:
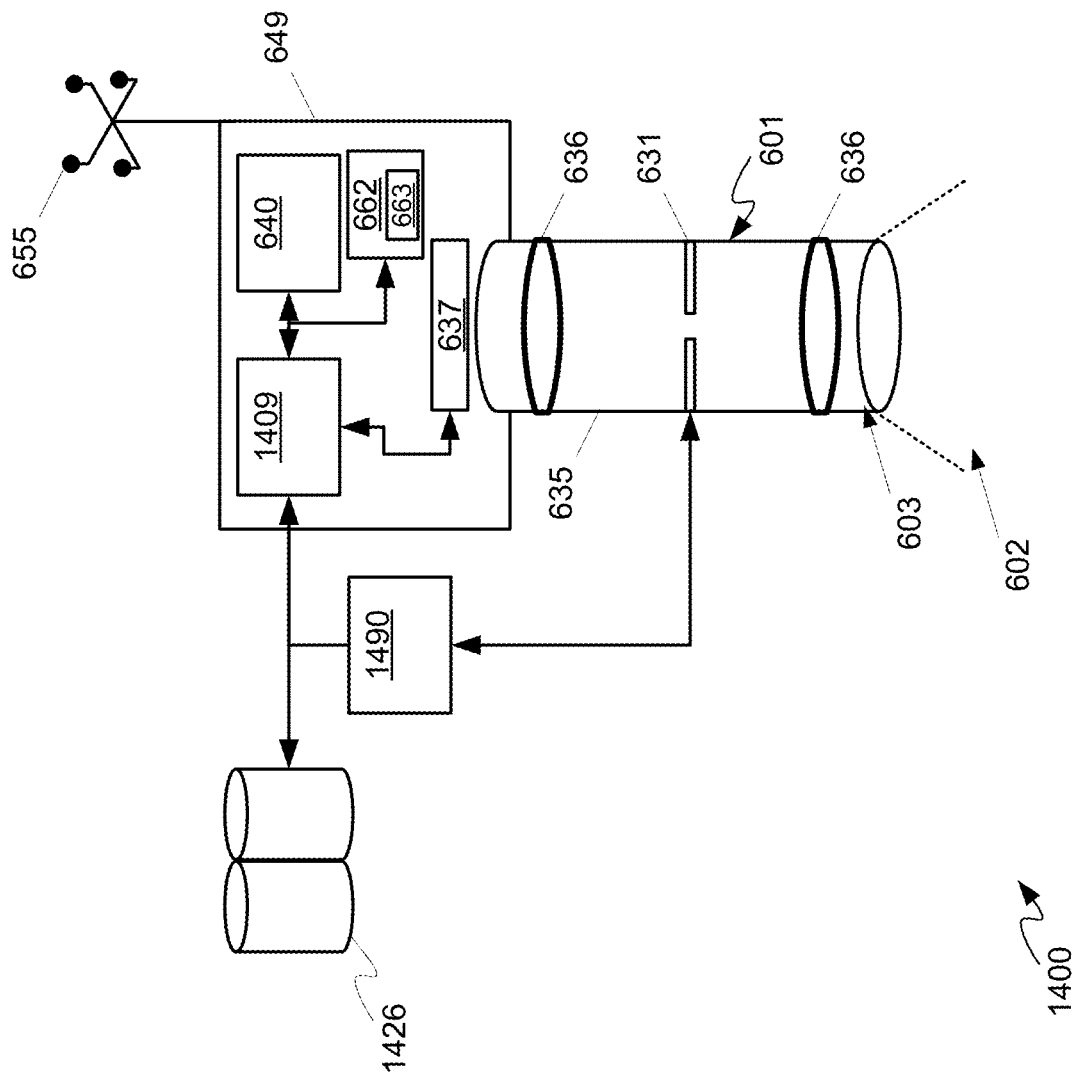

FIG. 14 depicts a schematic diagram of a camera system with automatic alternation between two numerical apertures and a stereo display device, according to non-limiting implementations.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however, persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Figure 1:
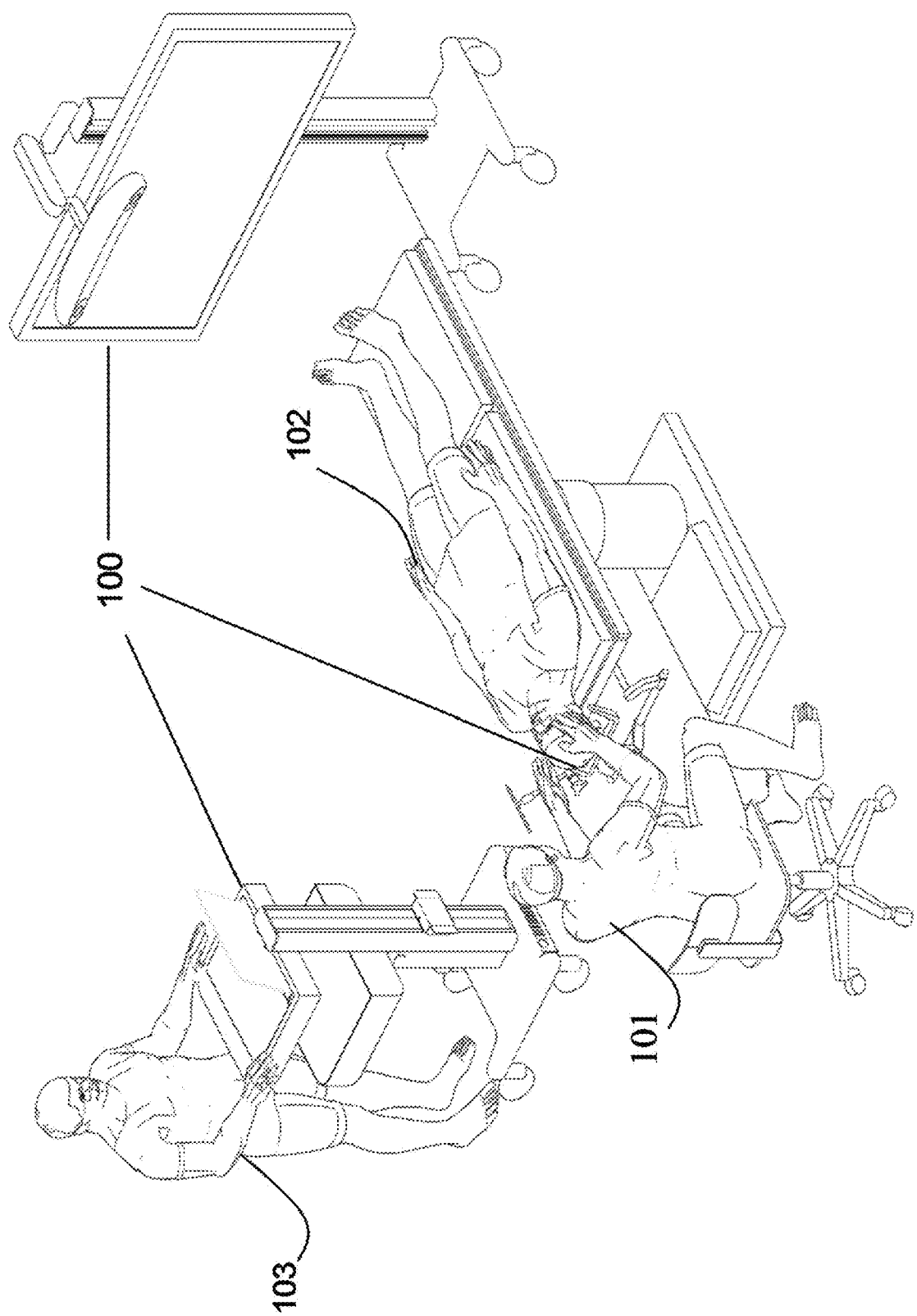
FIG. 1 shows an example operating room setup for a minimally invasive access port-based medical procedure, according to non-limiting implementations.

Referring to FIG. 1, a non-limiting example navigation system 100 is shown to support minimally invasive access port-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
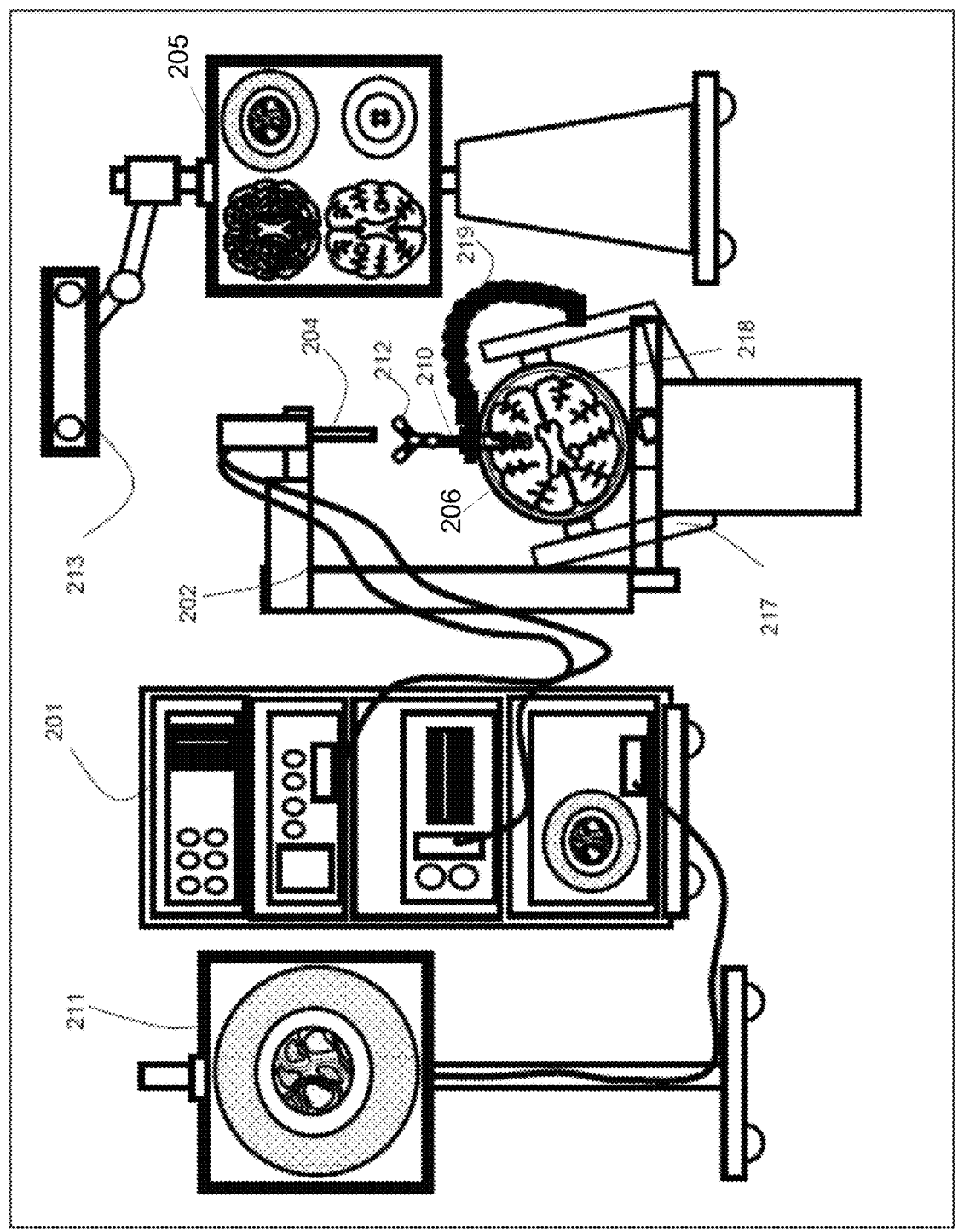
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
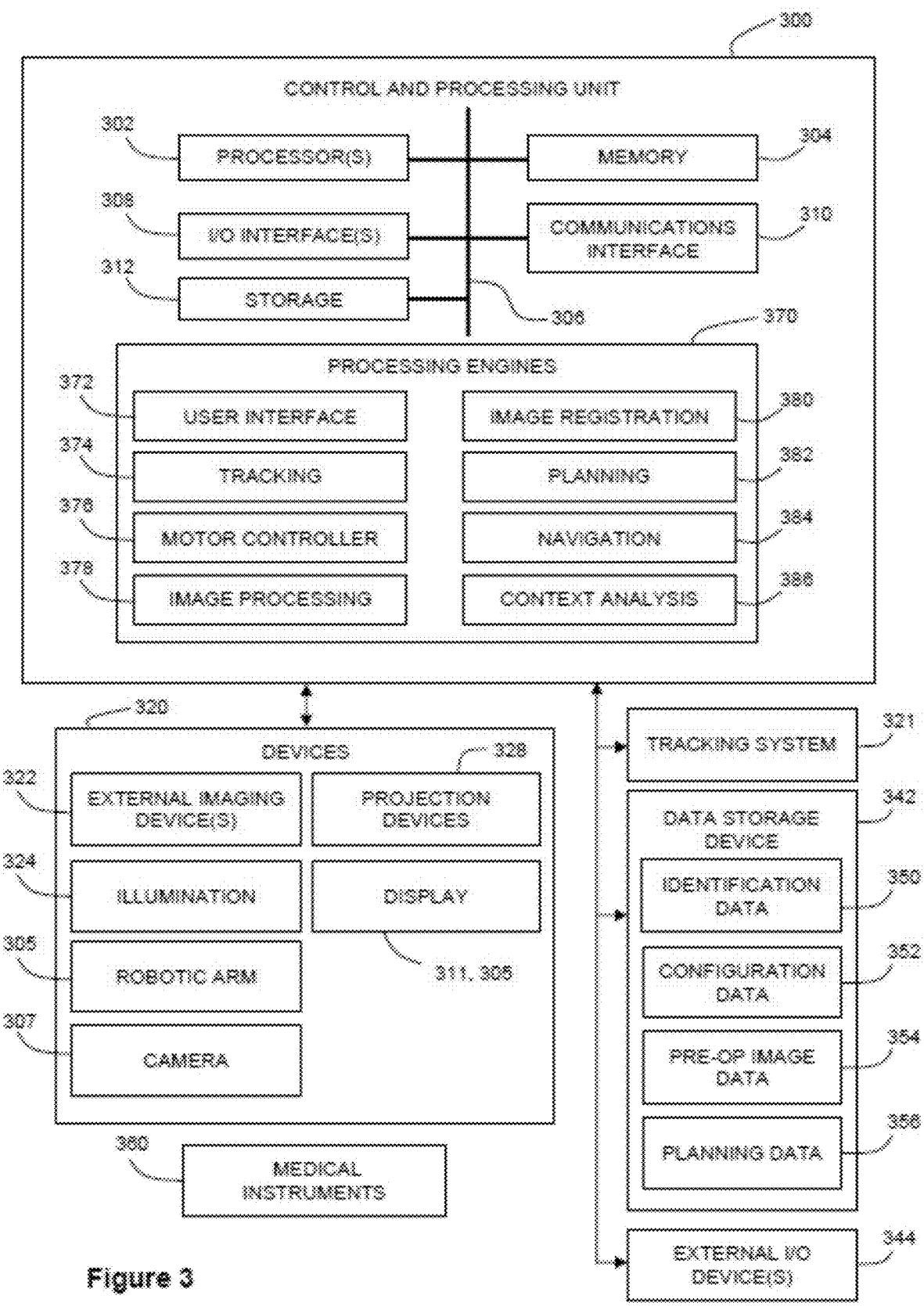
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, the one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited to, one or more external imaging devices 322, one or more illumination devices 324, a robotic arm, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
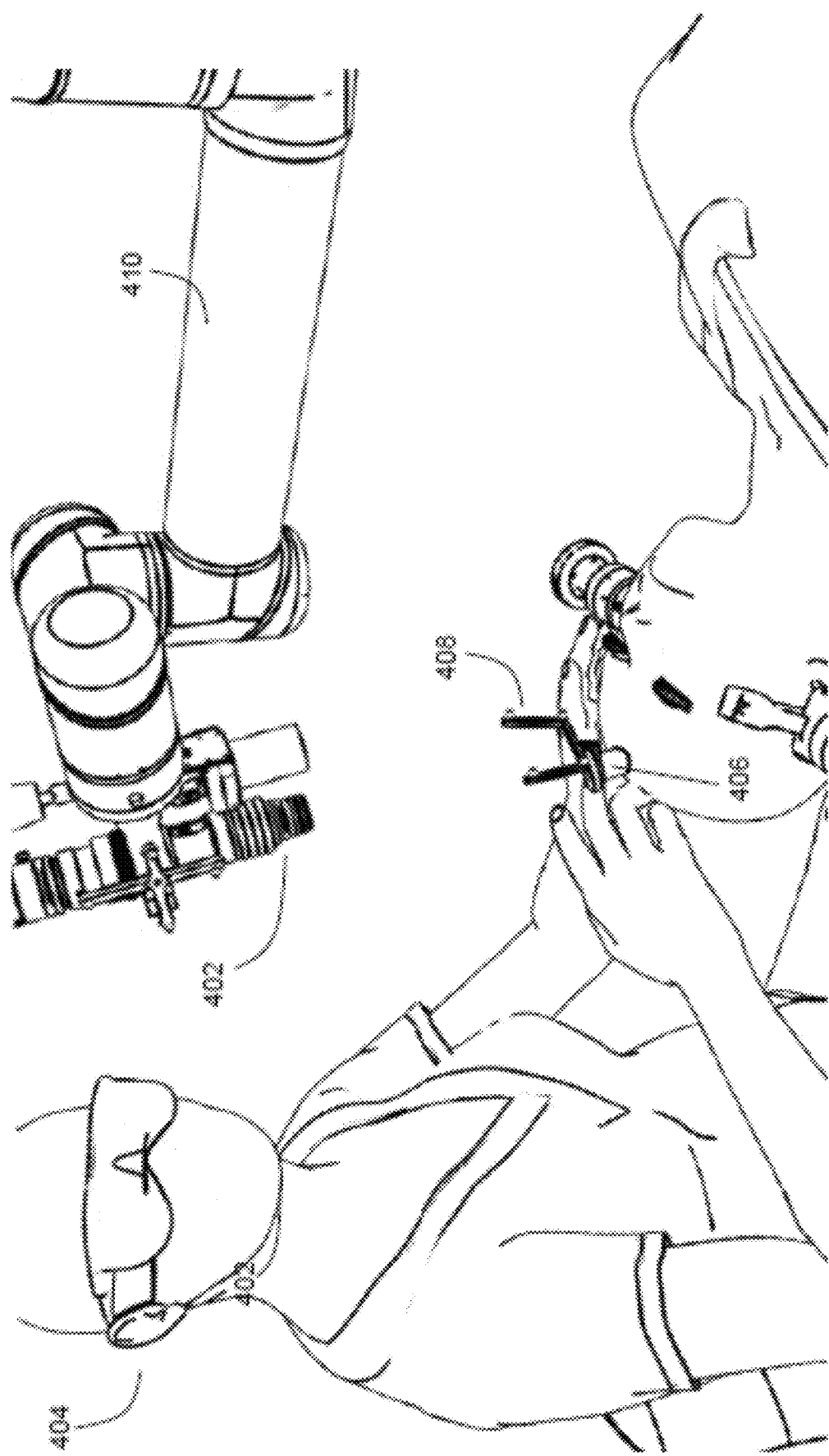
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
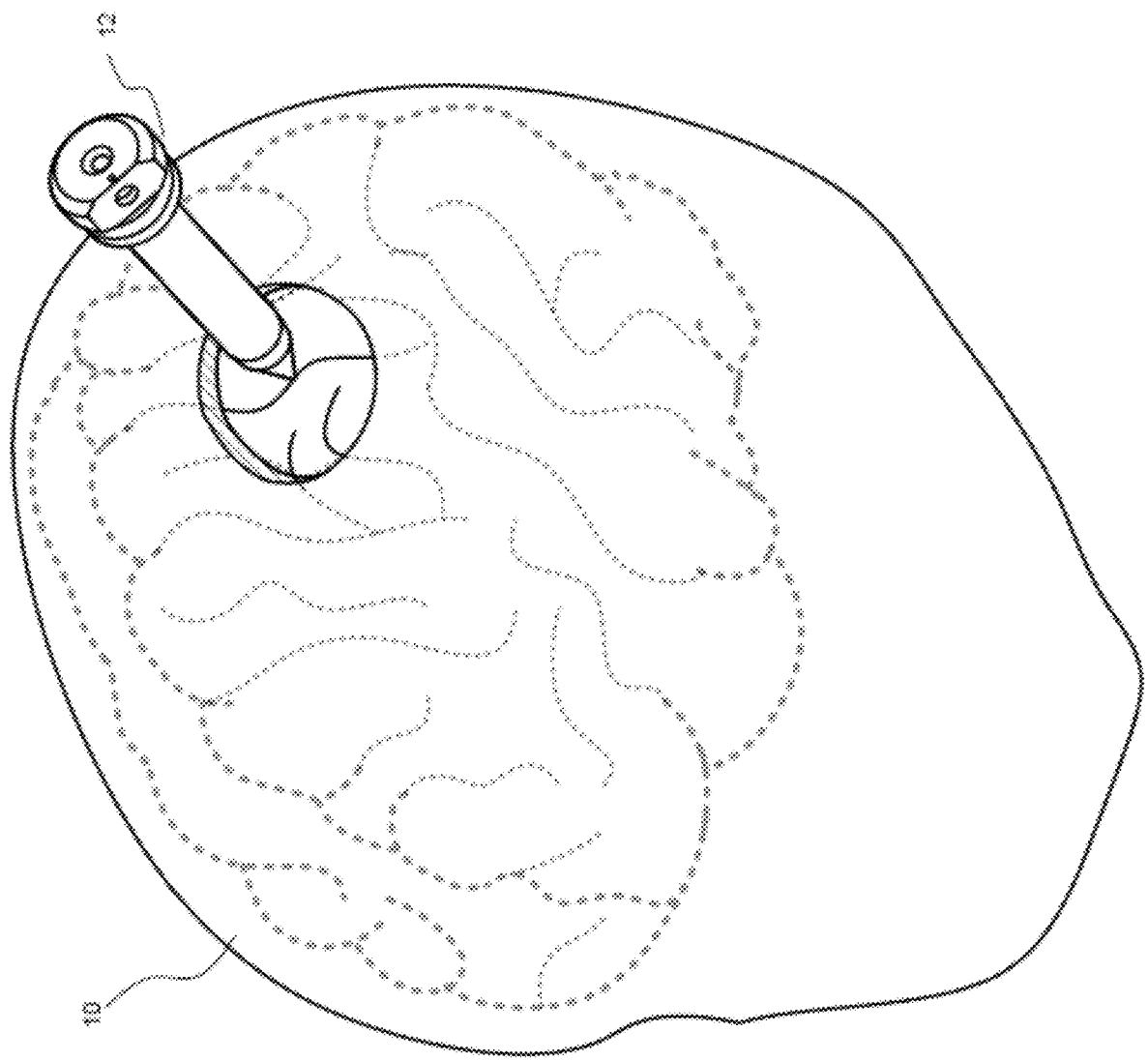
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Attention is next directed to FIG. 6, which depicts an example of a camera system that could be used with and/or in place of access port 12.

Specifically, FIG. 6 depicts a camera system 600 comprising: a camera device 601 having a field of view 602 (e.g. at a distal end 603), camera device 601 configured to automatically acquire: a first image of field of view 602 at a first numerical aperture; and a second image of field of view 602 at a second numerical aperture smaller than the first numerical aperture; an image processing unit 609 configured to combine the first image with the second image into a single image by: extracting a higher-resolution in-focus portion of the first image; and replacing a corresponding lower-resolution portion of the second image with the higher-resolution in-focus portion of the first image; and a display device 626 in communication with image processing unit 609, display device configured to render the single image. While the terms "first image" and "second image" are used throughout the present specification, such terms do not necessarily refer to an order of acquisition and the "second image" can be acquired before the "first image". Furthermore, while implementations are described in which system 600 is described with respect to a surgical camera system, system 600 can be used to image samples other than surgical samples.

It is assumed that the higher-resolution in-focus portion of the first image is located at an image plane of camera device 601 when the first aperture is used, and that the term "higher-resolution" with regards to the first image is relative to the second image; similarly, the term "lower-resolution" with regards to the second image is understood to be relative to the first image. In other words, as the second image is acquired at a second numerical aperture, smaller than a first numerical aperture used to acquire the first image, the resolution of the second image is lower as compared to the first image, but the depth-of-field of the second image is higher than that of the second image.

In other words, the, approximate formulas for each of depth of field (DOF) and a smallest feature that can be resolved (RES) for an optical system having a numerical aperture (NA) are:

$$DOF = \lambda / NA^2 \qquad \text{Equation (1)}$$

$$RES = 0.61 \lambda / NA \qquad \text{Equation (2).}$$

In each of Equation (1) and Equation (2), λ is the average wavelength of illumination light. Furthermore, RES indicates a smallest feature that can be resolved. Hence as NA of camera device 601 decreases (e.g. in the second image relative to the first image), a resolution of camera device 601 decreases as depth-of-field increases.

Furthermore, in the present specification, the terms proximal end and distal end will be used to refer to respective ends of components, with a proximal end being an end that will be proximal a surgeon and the like, when system 600 is in use, and a distal end being an end that will be distal the surgeon, and/or directed towards tissue, a sample, a patient being operated on, and the like, when system 600 is in use.

Furthermore, in the present application, the term aperture refers to one or more of a light transmissive area and/or an optically transmissive area which can include, but is not limited to, an opening, a hole, a gap, and the like, as well as areas of transmissive material such as glass, plastic and the like. Hence, the term aperture can alternatively be referred to as a light aperture. In contrast, the term numerical aperture refers to a dimensionless number that characterizes a range of angles over a the system can accept or emit light. Hence, for example, controlling a size of an aperture in an optical system changes a numerical aperture of the optical system.

As depicted, camera device 601 comprises a dynamic iris 631 configured to switch between the first numerical aperture and the second numerical aperture as described in further detail below with respect to FIG. 7. As depicted, camera device 601 further comprises a body 635, one or more lenses 636 (interchangeably referred to hereafter as lenses 636), and a sensor 637 in communication with image processing unit 609. While dynamic iris 631 is depicted as being located in body 635, dynamic iris 631 can be located anywhere before sensor 637 on a light path from distal end 603 to sensor 637, with the optics of system 600 and/or camera device 601 adapted accordingly.

In some implementations, body 635 can be configured for use with a surgical port (such as access port 12), such that system 600 can be used for port surgery; however, in other implementations body 635 can be configured for use in open surgery. Either way, system 600 can be configured for use in one or more port surgery, open surgery, and the like. As depicted, body 635 comprises a proximal end and a distal end 603, distal end 603 configured for positioning adjacent tissue in field of view 602 being imaged by camera device 601.

Further while body 635 is depicted as cylindrical, in other implementations, body 635 can comprise other shapes and in particular elongated shapes. Furthermore, body 635 can be of a diameter that enables surgical tools to be inserted down a same surgical port so that system 600 can be used to image tissue being operated upon. In some implementations, body 635 can be adapted to include external clips, vias and the like for use with surgical tools so that body 635 can be used to assist positioning of the surgical tools in the surgical port.

Lenses 636 can be located in body 635 and are generally configured to acquire light from field of view 602, convey the light through dynamic iris 631, which controls the numerical aperture of camera device 601, and convey the light to sensor 37. Indeed, lenses 636 can be located between dynamic iris 631 and sensor 637 and/or between dynamic iris 631 and distal end 603 of body 635. However, system 600 can comprise any suitable number and arrangement of lenses that enables acquisition of images by dynamic iris 631 and sensor 637. In particular, system 600 comprises an arrangement of lenses configured to focus light from a sample at a focusing plane onto sensor 637 via dynamic iris 631, which controls the numerical aperture of camera device 601.

Hence, in general, one or more lenses 636 focus light from a sample located at distal end 603 onto sensor 637 via dynamic iris 631. Sensor 637 can acquire images which are received at image processing unit 609 and/or buffered at an image buffering unit 640.

Sensor 637 can comprise an electronic imaging sensor including, but not limited to a charge coupled device (CCD); sensor 637 can hence acquire images which are received at image processing unit 609. Furthermore, sensor 637 can be configured to acquire images at a rate compatible with video, and hence camera device 601 can comprise a video device.

As depicted, system 600 can further comprise an image buffering unit 640 configured to one or more of buffer and sequence the first image and the second image acquired by camera device 601 at different numerical apertures, prior to processing and/or during processing by image processing unit 609, which provides a combined single image to display device 626. In other words, image buffering unit 640 can be in communication with image processing unit 609 and can be used by image processing unit 609 to produce combined images and/or an image stream provided to display device 626. As depicted, image processing unit 609 and image buffering unit 640 are housed in a common housing 649, and image processing unit 609 and image buffering unit 640 together can comprise a computing device.

In particular, image processing unit 609 and image buffering unit 640 can be configured to produce a video stream of images output to display device 626 and rendered thereupon. Indeed, image processing unit 609 can comprise a video processing unit and/or image buffering unit 640 can comprise a video processing unit.

Image processing unit 609 can be implemented as a processor and/or a plurality of processors, including but not limited to one or more central processors (CPUs) and/or one or more processing units and/or one or more graphic processing units (GPUs); either way, image processing unit 609 comprises a hardware element and/or a hardware processor. Indeed, in some implementations, image processing unit 609 can comprise an ASIC (application-specific integrated circuit) and/or an FPGA (field-programmable gate array) specifically configured to implement the functionality of image processing unit 609.

In other words, image processing unit 609 can be specifically adapted for providing images with simultaneous high resolution and large depth of field. Hence, image processing unit 609 is preferably not a generic computing device, but a device specifically configured to implement specific image production functionality. For example, image processing unit 609 can specifically comprise a computer executable engine configured to implement specific image production functionality, as described below.

As depicted, system 600 further comprises a memory 662 which can be combined with image buffering unit 640 or, as depicted, be separate from image buffering unit 640. Memory 662 can comprise a non-volatile storage unit (e.g. Erasable Electronic Programmable Read Only Memory ("EEPROM"), Flash Memory) and a volatile storage unit (e.g. random access memory ("RAM")). Programming instructions that implement the functional teachings of image processing unit 609 as described herein are typically maintained, persistently, in memory 662 and used by image processing unit 609 which makes appropriate utilization of volatile storage during the execution of such programming instructions. Those skilled in the art recognize that memory 662 is an example of computer readable media that can store programming instructions executable by image processing unit 609. Furthermore, memory 662 is also an example of a memory unit and/or memory module and/or a non-volatile memory.

Memory 662 can generally store an application 663 which, when processed by image processing unit 609, enables image processing unit 609 to combine a first image with a second image into a single image by: extracting a higher-resolution in-focus portion of the first image; and replacing a corresponding lower-resolution portion of the second image with the higher-resolution in-focus portion of the first image, as described below.

Image processing unit 609 is further configured to communicate with display device 626, which comprises any suitable one of, or combination of, flat panel displays (e.g. LCD (liquid crystal display), plasma displays, OLED (organic light emitting diode) displays, capacitive or resistive touchscreens, CRTs (cathode ray tubes) and the like. In some implementations, display device 626 comprises a heads up display (HUD) device worn, for example, by a surgeon and the like.

In some implementations, system 600 and/or image processing unit 609 can include a reference clock, for example for determining when to control dynamic iris 631 to a given numerical aperture.

While not depicted, in other implementations, system 600 can comprise one or more illumination sources to illuminate field of view 602 and specifically tissue from which images are being acquired; such illumination sources can be arranged to illuminate field of view 602 and/or an area adjacent distal end 603. Such one or more illumination sources can also be arranged to transmit light through body 635 and/or lenses 636 to illuminate field of view 602 and/or an area adjacent distal end 603. Either way, such illumination sources can include, but are not limited to, light emitting diodes. Furthermore, an average wavelength of such illumination sources can be used with each of Equation (1) and Equation (2) to respectively determine the DOF and RES parameters of system 600 and/or camera device 601.

Also depicted in FIG. 6 is an optional tracking device 655 attached to a proximal end of housing 649. In other words, as depicted, system 600 optionally comprises tracking device 655 configured to be tracked by a navigation system. Tracking device 655 is generally configured to be tracked by a navigation system external to system 600, for example a navigation system that is part of surgical system, such as that depicted in FIGS. 1 to 4. While not depicted housing 649 can further comprise a mount configured to removably attach tracking device 655 at a proximal end thereof (e.g. an end that is away from tissue being imaged). Tracking device 655 is generally positioned so that a camera, and the like, of a surgical navigation system may track a position of tracking device 655 and hence a relative position of distal end 603 of body 635. As depicted, tracking device 655 comprises four reflective spheres arranged in a configuration where each sphere is located at about a corner of a square. However, other numbers of spheres and other configurations are within the scope of present implementations. In particular or more of a number, arrangement, and configuration of such spheres may be selected to provide a given tracking accuracy, including, but not limited to, a tracking accuracy that is less than about half a diameter of a sensing array surface. However, tracking device 655 may include tracking devices other than reflective spheres. For example, in some implementations, tracking device 655 may include a flexible sheath configured to measure tip position deflection, for example deflection of a tip of the flexible sheath. Furthermore, system 600 can be adapted to include one or more tracking devices.

Furthermore, in some implementations, system 600 (other than display device 626) can comprise an optical scope similar to optical scope 204, which can be positioned with respect to a patient and/or tissue and/or a sample to be imaged using a device positioning system including, but not limited to, mechanical arm 202. Such positioning can occur using, in part, tracking device 655.

As depicted, system 600 further comprises an optional controller 690 which can be implemented as a processor and/or a plurality of processors, including but not limited to one or more central processors (CPUs) and/or one or more processing units and/or one or more graphic processing units (GPUs); either way, controller 690 comprises a hardware element and/or a hardware processor. Indeed, in some implementations, controller 690 can comprise an ASIC (application-specific integrated circuit) and/or an FPGA (field-programmable gate array) specifically configured to implement certain functionality of system 600.

For example, controller 690 can be specifically adapted for controlling dynamic iris 631 and/or coordinating positions of dynamic iris 631 with acquisition of images by image processing unit 609. In some implementations, controller 690 and image processing unit 609 can be combined. Either way, controller 690 is preferably not a generic computing device, but a device specifically configured to implement specific image production functionality. For example, image processing unit 609 can specifically comprise a computer executable engine configured to implement specific image production functionality, that includes controlling dynamic iris 631. In particular, controller 690 and/or image processing unit 609 can be a component of control and processing unit 300 including, but not limited to, one or more of processors 302.

Furthermore, while controller 690 is depicted as being in communication with dynamic iris 631 from a side of body 635, connections and/or communication between controller 690 and dynamic iris 631 can be through a proximal end of body 635, for example, and not through a side of body 635. Alternatively, connections and/or communication between controller 690 and dynamic iris 631 can occur using image processing unit 609.

Figure 7:
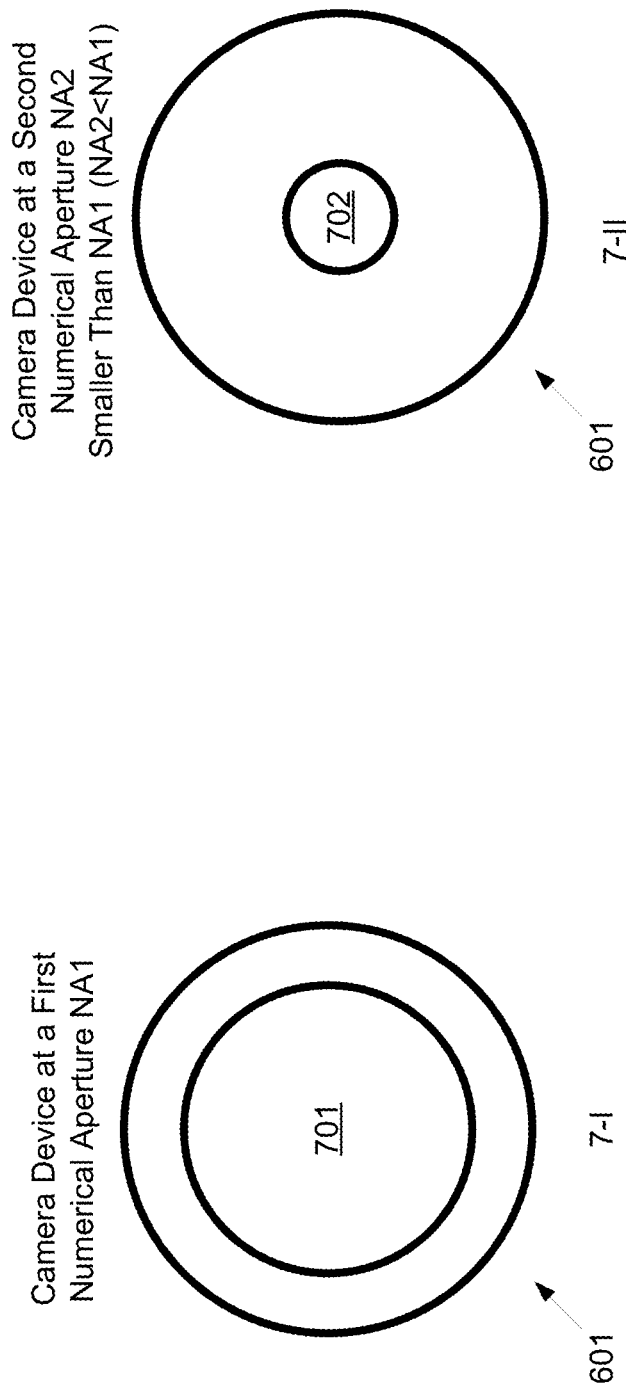
FIG. 7 depicts an end view of a camera device of the system of FIG. 6 and showing two aperture positions of the camera system of FIG. 6, according to non-limiting implementations.

For example, attention is directed to FIG. 7 which depicts and end view of camera device 601 (e.g. from distal end 903) in a first configuration 7-I and a second configuration 7-II. In the first configuration 7-I, camera device 601 has a larger numerical aperture NA1 compared to a numerical aperture NA2 of the second configuration 7-II. For example, an aperture of dynamic iris 631 can decrease from a first aperture size 701 in the first configuration 7-I to a second aperture size 702 in the second configuration 7-II. Hence in the second configuration 7-II the depth of field of camera device 601 will be larger than in the first configuration 7-I, but the resolution of camera device 601 in the second configuration 7-II will be smaller than in the first configuration 7-I, as understood from Equation (1) and Equation (2).

Various devices for changing the numerical aperture of camera device 601 are within the scope of present implementations are described below. However, operation of system 600 is next described with reference to FIG. 8 to FIG. 9.

Attention is now directed to FIG. 8 which depicts a block diagram of a flowchart of a method 800 of controlling system 600 to acquire and combine images at different numerical apertures, according to non-limiting implementations. In order to assist in the explanation of method 800, it will be assumed that method 800 is performed using system 600, including image processing unit 609 and/or another processor and/or controller 690 controlling system 600 including dynamic iris 631 and sensor 637. Indeed, method 800 is one way in which system 600 can be configured. Furthermore, the following discussion of method 800 will lead to a further understanding of system 600, and its various components. However, it is to be understood that system 600 and/or method 800 can be varied, and need not work exactly as discussed herein in conjunction with each other, and that such variations are within the scope of present implementations.

Regardless, it is to be emphasized, that method 800 need not be performed in the exact sequence as shown, unless otherwise indicated; and likewise various blocks may be performed in parallel rather than in sequence; hence the elements of method 800 are referred to herein as "blocks" rather than "steps". It is also to be understood, however, that method 800 can be implemented on variations of system 600 as well.

At block 801, image processing unit 609, and the like, controls camera device 601 to acquire a first image at a first numerical aperture.

At block 803, image processing unit 609, and the like, controls camera device 601 to acquire a second image at a second numerical aperture smaller than the first numerical aperture, for example using the same field of view at which the first image was acquired at block 801. In other words, camera device 601 is controlled to acquire each of the first image and the second image using a common field of view.

It is further appreciated that blocks 801, 803 can be performed in any order and/or can be performed on an on-going basis such that a video-stream from camera device 601 comprises alternating images of the common field of view, and the images can be buffered at image buffering unit 640.

At block 805, image processing unit 609, and the like, extracts a higher-resolution in-focus portion of the first image.

At block 807, image processing unit 609, and the like, replaces a corresponding lower-resolution portion of the second image with the higher-resolution in-focus portion of the first image.

At block 809, image processing unit 609, and the like, outputs a combined single image that results from blocks 805, 807 to display device 626.

Method 800 will now be described with reference to FIG. 9 which depicts a first image 901 acquired at block 801 using a first numerical aperture of camera device 601, for example numerical aperture NA1 of FIG. 7. First image 901 comprises several features including an in-focus portion 903 and an out-of-focus portion 905. Hence, it is assumed that camera device 601 is focussed at an image plane and that an object of interest, such as tissue and the like, is located at the image plane, such that in-focus portion 903 comprises an image focussed on the object of interest. It is further assumed that out-of-focus portion 905 includes objects that are not located out of the image plane and hence out-of-focus portion 905 comprises images of such object that are out of focus. While each of in-focus portion 903 and out-of-focus portion 905 are depicted as being in particular areas of first image 901 each of in-focus portion 903 and out-of-focus portion 905 can be located anywhere in first image 901, and furthermore each of in-focus portion 903 and out-of-focus portion 905 can comprise a plurality of areas of first image 901. In other words, more than one object can be in-focus, while the remaining objects are out of focus.

Furthermore, to indicate the object of in-focus portion 903 being in-focus, the object of in-focus portion 903 is depicted in solid lines; similarly, to indicate the objects of out-of-focus portion 905 being out of focus, the objects of out-of-focus portion 905 are depicted in stippled lines.

FIG. 9 also depicts a second image 912 acquired at block 803 using a second numerical aperture of camera device 601, for example numerical aperture NA2 of FIG. 7, the second numerical aperture being smaller than the first numerical aperture used to acquire first image 901. Furthermore, as second image 912 shares a common field of view with first image 901 (e.g. field of view 602), second image 912 comprises the same features of first image 901. Hence, for example, second image 912 can comprise: a first portion 913 corresponding to in-focus portion 903; and a second portion 915 corresponding to out-of-focus portion 905. However, the second numerical aperture NA2 of camera device 601 is selected such that each of first portion 913 and second portion 915 are in focus and/or the second numerical aperture NA2 of camera device 601 is selected such that at least second portion 915 is in focus. In other words, as the second numerical aperture NA2 of camera device 601 used to acquire second image 912 is smaller than the first numerical aperture NA1 of camera device 601 used to acquire first image 901, the depth of field of second image 912 is larger than the depth of field of first image 901. Indeed, second numerical aperture NA2 can be selected such that all objects in field of view 602 of camera device 601 are in focus in a particular use-situation (e.g. use in surgery compatible with access port 12). Similarly, first numerical aperture NA1 can be selected such that only an object-of-interest (e.g. tissue on which surgery is to occur) in field of view 602 of camera device 601 is in focus in the same particular use-situation. For example, a surgeon, and the like, interacting with controller 690 can use optional controller 690 to select a depth-of-field, and numerical apertures of camera device 601 can be adjusted accordingly. In addition, one or more pointers of a tracking system in use with system 600 can be used to point at two different depths of a sample to determine a depth-of-field and numerical apertures of camera device 601 can be adjusted accordingly.

However, a resolution of second image 912 will be lower than a resolution of first image 901 (e.g. as numerical aperture NA2 is smaller than numerical aperture NA1) and hence while all objects of second image 912 can be in focus, their resolution will be smaller than that of corresponding objects in first image 901. Hence, to indicate that all objects of second image 912 are in focus, but of a smaller resolution than objects in first image 912, objects in each first portion 913 and second portion 915 each drawn in stippled lines that are coarser than the stippled lines of objects used in out-of-focus portion 905.

FIG. 9 further depicts an arrow 919 between in-focus portion 903 of first image 901 and first portion 913 of second image 912 indicating that first portion 913 of second image 912 corresponds to in-focus portion 903 of first image 901.

Hence, as in-focus portion 903 of first image 901 comprises a higher-resolution in-focus portion of first image 901, at block 807 image processing unit 609 extracts higher-resolution in-focus portion 903 of first image 901 and, at block 809, image processing unit 609 replaces a corresponding lower-resolution portion 913 of second image 912 with the higher-resolution in-focus portion 903 of first image 901. For example, image processing unit 609 produces a combined single image 922 comprising in-focus portion of first image 901 and second portion 915 of second image 912.

Hence, image processing unit 609 is generally configured to determine the higher-resolution in-focus portion 903 of first image 901 using any suitable algorithm for identifying in-focus portions of image. Such algorithms can include, but are not limited to, one or more contrast analysis algorithms. For example, contrast of each of first image 901 and second image 912 can be compared to determine contours of relative contrast changes to determine in-focus portion 903 of first image 901. However, other techniques for identifying in-focus portions of an image are within the scope of present implementations, including, but not limited to a surface scanning technique used in conjunction with known navigated distances on a sample. For example, a sample can be initially scanned over a known distance to determine a topology of the sample using a scanning device and/or system 600 at a fixed aperture size; once a topology of the sample is known, using known depths-of-field each numerical aperture of system 600, it can be determined which regions of a sample should be in focus (and which regions will not).

Furthermore, image processing unit 609 is generally configured to determine a portion 913 of second image 912 that corresponds to in-focus portion 903; for example, once coordinates of pixels of in-focus portion 903 have been determined, such coordinates can be used to replace corresponding pixels of second image 912 with pixels of in-focus portion 903 to produce combined single image 922. However, any suitable method and/or algorithm can be used to replace first portion 913 with in-focus portion 903. For example, the contours of relative contrast changes to determine in-focus portion 903 of first image 901 can be used.

Returning briefly to FIG. 6 and FIG. 7, camera device 601 comprises a dynamic iris 631 configured to switch between the first numerical aperture NA1 and the second numerical aperture NA2. For example, in some implementations, camera device 601 and/or dynamic iris 631 can comprise a transmissive display device configured to form a first light aperture (e.g. as in configuration 7-I of FIG. 7), defining the first numerical aperture NA1, and a second light aperture (e.g. as in configuration 7-II of FIG. 7), defining second numerical aperture NA2. For example, as clearly seen in FIG. 7, a diameter of the first light aperture (e.g. as in configuration 7-I of FIG. 7) is larger than a respective diameter of the second light aperture (e.g. as in configuration 7-II of FIG. 7). Further, controller 690 (and the like) can be configured to automatically switch the transmissive display device between the first light aperture and the second light aperture, such that first image 901 is automatically acquired using the first light aperture and second image 912 is automatically acquired using the second light aperture.

Furthermore, such a transmissive display device can be controlled to move between aperture sizes continuously and/or semi-continuously, such that method 800 can be implemented continuously and/or semi-continuously, at image processing unit 609 to provide a "real-time" image of objects in field of view 602.

It is further understood that, in these implementations, the term "aperture" refers to a region that is transmissive and/or at least partially transparent to light, but is not necessarily a hole, and the like. Rather, apertures formed by a transmissive display device can simply be regions that are controlled to transmit light, but otherwise are integral with the remainder of the transmissive display device.

For example, such a transmissive display device can include, but is not limited to, a transmissive liquid crystal display (LCD) which can be located in body 635 and/or at a proximal end of body 635, and at least before sensor 637, with optics of system 600 and/or camera device 601 adapted accordingly. In other words, a portion of the transmissive LCD in the region of the aperture can be controlled to be transmissive, while a portion of the transmissive LCD in the region outside the aperture can be controlled to be non-transmissive. The transmissive region can be controlled to increase or decrease (e.g. by controller 690, and the like) to control (with reference to FIG. 7) the size 701, 702 of the aperture and hence the numerical aperture of system 600 and/or camera device 601.

Alternatively, such a transmissive display device can include, but is not limited to, a transmissive organic light emitting device (OLED) display. Similar to the transmissive LCD, a portion of the transmissive OLED in the region of the aperture can be controlled to be transmissive, while a portion of the transmissive OLED in the region outside the aperture can be controlled to be non-transmissive. The transmissive region can be controlled to increase or decrease (e.g. by controller 690, and the like) to control (with reference to FIG. 7) the size 701, 702 of the aperture and hence the numerical aperture of system 600 and/or camera device 601. Furthermore, as OLED displays are emissive (e.g. pixels of OLED materials emit light), a dynamic iris that includes an OLED display can be used as an illumination source, as well as to control a numerical aperture of camera device 601.

For example, attention is directed to FIG. 10, which depicts a camera device 1001 that is substantially similar to camera device 601, with like elements having like numbers, however camera device 1001 includes an emissive dynamic iris 1031 that emits light, which can include, but is not limited to, an OLED display. In particular, FIG. 10 depicts emissive dynamic iris 1031 in a first configuration 10-I, corresponding to first configuration 7-I of FIG. 7, and a second configuration 10-II, corresponding to second configuration 7-II of FIG. 7. Hence, in first configuration 10-I, an aperture (and a numerical aperture) of camera device 1001 is larger than an aperture (and a numerical aperture) of camera device 1001 in second configuration 10-II.

Hence, an area of emissive dynamic iris 1031 that is outside of the aperture in the first configuration 10-I is smaller than the area of first configuration 10-I that is outside of the aperture in the second configuration 10-II.

Presuming that the area of emissive dynamic iris 1031 is emissive (e.g. emissive dynamic iris 1031 can comprise an OLED display and/or OLED pixels and/or any other device where with a light emissive area that can be controlled in size to change a size of an aperture there through), the portion of the emissive dynamic iris 1031 in the region outside the aperture that can be controlled to be non-transmissive can also be controlled to emit illumination light to illuminate field of view 602. In configuration 10-I, emissive dynamic iris 1031 emits light 1051 while in configuration 10-II, emissive dynamic iris 1031 emits light 1052. Light 1051 is emitted from a smaller area of emissive dynamic iris 1031 than light 1052, as the size of aperture decreases from configuration 10-I to configuration 10-2 (e.g. the region of emissive dynamic iris 1031 outside of the aperture increases from configuration 10-I to configuration 10-2), but the total light emitted can remain about constant from configuration 10-I to configuration 10-II. Hence, for example, an integration of light 1051 can result in about the same total amount of an integration of light 1052. Hence, for example, the light emitted per unit area in configuration 10-II can decrease relative to configuration 10-I, but the total light emitted can be about the same between configuration 10-I and configuration 10-II. Hence, in example implementations, both images 901, 912 will have a similar and/or the same brightness.

Put another way, the aperture decreases from a larger size in configuration 10-I to a smaller size in configuration 10-II, the portion of the emissive dynamic iris 1031 in the region outside the aperture decreases in area. Hence, as the aperture decreases, the portion of the emissive dynamic iris 1031 in the region outside the aperture can be controlled to decrease in brightness to maintain a given brightness in field of view 602. Similarly, the aperture increases from a smaller size in configuration 10-II to a larger size in configuration 10-II, the portion of the emissive dynamic iris 1031 in the region outside the aperture increases in area. Hence, as the aperture increases, the portion of the emissive dynamic iris 1031 in the region outside the aperture can be controlled to increase in brightness to maintain a given brightness in field of view 602. Again, in example implementations, both images 901, 912 will have a similar and/or the same brightness.

However, in other processes and/or mechanisms for maintaining a given brightness at a sample are within the scope of present implementations. However, in other processes and/or mechanisms for maintaining a given brightness at a sample and/or at sensor 637 are within the scope of present implementations. In particular, when aperture size changes (e.g. of dynamic iris 631), the amount of light that reaches a sample, and hence sensor 637 also changes; hence, images

901, 912 can have different brightness levels unless compensation occurs. Present implementations can include one or more of the following brightness compensations schemes:

a) Modulating gain of sensor 637 (or any other sensor described herein) such that the gain is more sensitive for low light aperture situations (e.g. when dynamic iris 631 is controlled to a smaller aperture).

(b) Image processing where brightness of one or more of image 901, 912 is digitally adjusted.

(c) Neutral density optical filters that mechanically attached to larger apertures, for example, when a dynamic iris includes two types of aperture of fixed relative sizes (e.g. see implementations described below with respect to FIG. 11 and FIG. 12).

(d) For implementations that include a transmissive LCD aperture, relative brightness can be controlled using using liquid crystals.

(e) A variable neutral density filter incorporated into dynamic iris 631 and/or body 635 (e.g. before and/or after dynamic iris 631), configured for variable neutral density transmission filter; such a variable neutral density filter can be based on liquid crystals.

Furthermore, other image processing techniques that are specific to a given numerical aperture and/or aperture size are within the scope of present implementations. For example, each of images 901, 912 can have different types of distortions due to the different numerical aperture used to acquire each of images 901, 912. Hence, different distortion correction image processing can occur for each of images 901, 912, and/or images processing specific to each numerical aperture can be applied to respective images acquired with each numerical aperture to correct for distortions that are unique to each numerical aperture. Indeed, in tests of systems having different numerical apertures, it was notes that images acquired with different numerical apertures may not be exactly spatially correlated as the different numerical apertures can warp images differently. However, as system 600 can be modelled for each numerical aperture used therewith, such models can be used to generate distortion corrections, assuming, for example, working distances and/or focus distances are determined.

Other implementations of a dynamic iris are within the scope of present implementations. For example, attention is next directed to FIG. 11, which depicts a device 1100 that can be used in camera device 601 as a dynamic iris. In particular, device 1100: a plate 1101 including a first aperture 1131, defining a first numerical aperture, and a second aperture 1132, defining a second numerical aperture, a diameter of first aperture 1131 being larger than a respective diameter of second aperture 1132; and an actuator 1157 configured to automatically move plate 1101 relative to field of view 602 of camera device 601 such that a first image (e.g. first image 901) is automatically acquired using first aperture 1131 and a second image (e.g. second image 912) is automatically acquired using second aperture 1132 and combined as described above. To maintain a similar brightness between the two apertures 1131, 1132, a neutral density filter can be incorporated into the larger aperture 1131. A variable neutral density filter could alternatively be used.

Hence, for example, actuator 1157 can comprise a coil actuator, and the like, with plate 1101 attached to an arm 1160 thereof, and the coil actuator can move arm 1160 to, in turn, move plate 1101, as indicated by arrow 1170. Furthermore, plate 1101 is positioned such that first aperture 1131 and second aperture 1132 move between two positions such that in a first position first aperture 1131 defines the numerical aperture of camera device 601 (e.g. similar to configuration 7-I of FIG. 7), and in a second position second aperture 1132 defines the numerical aperture of camera device 601 (e.g. similar to configuration 7-II of FIG. 7).

Furthermore, actuator 1157 can continue to move plate 1101 between the positions such that method 800 is implemented continuously and/or semi-continuously, at image processing unit 609 to provide a "real-time" image of objects in field of view 602.

It is understood that device 1100 can be manufactured to be of a size compatible with body 635, and hence device 1100 can include, but is not limited to, a MEMS (microelectromechanical system). Furthermore, body 635 and/or a physical footprint of device 1100 can be adapted for use with an access port (including, but not limited to, access port 12), and the like, and/or port-based surgery.

Yet further implementations of a dynamic iris are within the scope of present implementations. For example, attention is next directed to FIG. 12, which depicts a device 1200 that can be used in camera device 601 as a dynamic iris. In particular, device 1200: a plate 1201 including at least one first aperture 1231, defining a first numerical aperture, and at least one second aperture 1232, defining a second numerical aperture, a diameter of at least one first aperture 1231 being larger than a respective diameter of at least one second aperture 1232; and an actuator 1257 configured to automatically move plate 1201 relative to field of view 602 of camera device 601 such that a first image (e.g. first image 901) is automatically acquired using at least one first aperture 1231 and a second image (e.g. second image 912) is automatically acquired using at least one second aperture 1232. To maintain a similar brightness between the two types apertures 1231, 1232, a neutral density filter can be incorporated into each of the larger aperture 1231. A variable neutral density filter could alternatively be used.

However, in contrast to device 1100, in device 1200, plate 1201 is circular with a plurality of first apertures 1231 and a plurality of second apertures 1232 arranged alternately around an edge of plate 1201. In other words, apertures of plate 1201 alternative between a first aperture 1231 and a second aperture 1232. Furthermore, actuator 1257 can comprise a motor and/or direct current (DC) motor, and/or a stepper motor which with an axle thereof attached to a centre of plate 1201, such that actuator 1257 rotates plate 1201.

Hence, for example, plate 1201 is positioned such that, as plate 1201 rotates, each of aperture 1231, 1232 are rotated into positions where each define, in a sequence, the numerical aperture of camera device 601. For example, the numerical aperture is changed between configuration 7-I and configuration 7-II as plate 1201 rotates. First images (e.g. similar to first image 901) and second images (e.g. similar to second image 912) are acquired at each position and combined as described above.

Furthermore, actuator 1257 can continue to rotate plate 1201 between the positions such that method 800 is implemented continuously and/or semi-continuously, at image processing unit 609 to provide a "real-time" image of objects in field of view 602.

It is understood that device 1200 can be manufactured to be of a size compatible with body 635, and hence device 1200 can include, but is not limited to, a MEMS. Furthermore, body 635 and/or a physical footprint of device 1200 can be adapted for use with an access port (including, but not limited to, access port 12), and the like, and/or port-based surgery.

It is further understood that other mechanisms for adjusting numerical aperture are within the scope of present implementations, including, but not limited to, other types of MEMS-based devices and/or other types of mechanical devices and/or other types of display devices and/or other types of optical devices.

For example, attention is next directed to FIG. 13 which depicts a camera device 1301 that is substantially similar to camera device 601, with like elements having like numbers. However, camera device 1301 includes a first sensor system 1234-1 having a first aperture 1235-1 defining a first numerical aperture for images acquired by a first sensor 1237-1 (similar to sensor 637); a second sensor system 1234-2 having a second aperture 1235-2 defining a second numerical aperture for images acquired by a second sensor 1237-2 (also similar to sensor 637); and a beam splitter 1240 configured to split light from field of view 602 between the first sensor system 1234-1 and the second sensor system 1234-2. For example, each of apertures 1235-1, 1235-2 can be fixed, but of different sizes, with, for example, aperture 1235-1 corresponding to first configuration 7-I of FIG. 7, and aperture 1235-2 corresponding to first configuration 7-II of FIG. 7, with each of sensor 1237-1, 1237-2 acquiring images as described above. Using camera device 1301, sensor 1237-1 can acquire a first image, similar to first image 901, and sensor 1237-2 can acquire a second image, similar to second image 912, and an image processing unit (e.g. image processing unit 609) can implement method 800 using images from each sensor 1237-1, 1237-2.

Alternatively, each of apertures 1235-1, 1235-2 can comprise any of the dynamic irises (including, but not limited to devices 1100, 1200), as described above, to provide further flexibility.

Beam splitter 1240 is arranged at a proximal end of body 635 and is configured and/or positioned to about equally split light from field of view 602, as collected by lenses 636 between systems 1234-1, 1234-2. Any type of beam splitter is within the scope of present implementations including, but not limited to, a dynamic beam splitter that can be controlled (e.g. by controller 690) to direct light to one of systems 1234-1, 1234-2 such that depth of field and resolution of images, and/or portions of images, output to a display device 626 can be controlled using one or both of systems 1234-1, 1234-2. For example, when one or both of apertures 1235-1, 1235-2 are dynamic and beam splitter 1240 is also dynamic, then depth of field and/or resolution of at least two portions images output to a display device can be controlled and/or combined independent of one another.

Yet further implementations are within the scope of the present specification. For example, any of the systems and/or camera devices described herein can be configured to switch between a first numerical aperture and a second numerical aperture at a given rate, such that a first image and a second image are acquired at a rate half of the given rate, and the single image generated from the first image and the second image is generated at half the given rate. For example, a given rate can be at least 60 Hz such the first image and the second image are each acquired at a rate of at least 30 Hz, and similarly a single image generated from the first image and the second image can be generated at a rate of at least 30 Hz. In particular, an image acquisition rates can be used that are compatible with video rates at a display device of systems described herein and/or compatible with rates where a human vision does not detect flicker.

Yet further implementations are within the scope of present implementations. For example, attention is directed to FIG. 14 which depicts a system 1400 which is substantially similar to system 600, with like elements having like numbers. In particular, system 1400 comprises a display device 1426 that includes a stereo three-dimensional display device and/or a binocular device comprising a two displays arranged to provide stereo images to a human vision system. Furthermore, system 1400 comprises an image processing device 1409 and/or a controller 1490 configured to: provide a first image from camera device 601, acquired at a first numerical aperture, to a first one of the displays of display device 1426; and provide a second image from camera device 601, acquired at a second numerical aperture smaller than the first numerical aperture, to a second one of the displays of display device 1426. For example, images similar to images 901, 912 can be provided at different displays of display device 1426 such that a human looking into display device 1426 combines the images visually and/or with their brain. Hence, in contrast to system 600, portions of images are not extracted and/or replaced as in method 800. Rather images acquired by camera device 601 at two different numerical apertures are provided in a stereo arrangement in display device 1416.

In any event, a camera system is provided that includes a camera device that can be controlled between two numerical apertures, and images acquired at each numerical can be combined to provide a higher resolution portion of interest with a lower resolution background.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A camera system comprising:
   a camera device having a field of view, the camera device configured to automatically acquire:
   a first image of the field of view at a first numerical aperture, the first image comprising: an in-focus portion; and an out-of-focus portion; and
   a second image of the field of view at a second numerical aperture smaller than the first numerical aperture, the first image being of a higher resolution than the second image, the second image comprising: a first portion corresponding to the in-focus portion of the first image; and a second portion corresponding to the out-of-focus portion of the first image, the second portion being in focus;
   the field of view being a common field of view for both the first image acquired using the first numerical aperture and the second image acquired using the second numerical aperture, the first portion and the second portion of the second image comprising same respective features as the in-focus portion and the out-of-focus portion of the first image in the common field of view,
   the camera device comprising:
   a plate including a first aperture, defining the first numerical aperture, and a second aperture, defining the second numerical aperture, a diameter of the first aperture being larger than a respective diameter of the second aperture; and
   an actuator configured to automatically move the plate relative to the field of view of the camera device such that the first image is automatically acquired using the first aperture and the second image is automatically acquired using the second aperture;
   an image processing unit configured to combine the first image with the second image into a single image by:

extracting the in-focus portion of the first image; and
replacing the first portion of the second image with the in-focus portion of the first image; and, a display device in communication with the image processing unit, the display device configured to render the single image, the single image being a video image.

2. The camera system of claim 1, wherein the camera device is configured to switch between the first numerical aperture and the second numerical aperture at a given rate, such that the first image and the second image are acquired at a rate half of the given rate, and the video image is generated at half the given rate.

3. The camera system of claim 2, wherein the given rate is at least 60 Hz.

4. The camera system of claim 1, wherein the image processing unit is further configured to determine the in-focus portion of the first image using one or more contrast analysis algorithms.

5. The camera system of claim 1, further comprising a tracking device configured to be tracked by a navigation system.

6. A method comprising:
at a system comprising: a camera device having a field of view and configured to change between at least two numerical apertures, the camera device comprising: a plate including a first aperture, defining a first numerical aperture, and a second aperture, defining a second numerical aperture, a diameter of the first aperture being larger than a respective diameter of the second aperture; and an actuator configured to automatically move the plate relative to the field of view of the camera device such that a first image is automatically acquired using the first aperture and a second image is automatically acquired using the second aperture, the field of view being a common field of view for both the first image acquired using the first numerical aperture and the second image acquired using the second numerical aperture, the first image comprising: an in-focus portion; and an out-of-focus portion, and the first image being of a higher resolution than the second image, the second image comprising: a first portion corresponding to the in-focus portion of the first image; and a second portion corresponding to the out-of-focus portion of the first image, the second portion being in focus, the first portion and the second portion of the second image comprising same respective features as the in-focus portion and the out-of-focus portion of the first image in the common field of view; an image processing unit; and a display device in communication with the image processing unit,
acquiring, using the camera device, the first image of the field of view at the first numerical aperture;
acquiring, using the camera device, the second image of the field of view at the second numerical aperture smaller than the first numerical aperture;
combining, using the image processing unit, the first image with the second image into a single image by:
extracting the in-focus portion of the first image; and
replacing the first portion of the second image with the in-focus portion of the first image; and,
rendering, at the display device, the single image, the single image being a video image.

7. The method of claim 6, wherein the camera device is configured to switch between the first numerical aperture and the second numerical aperture at a given rate, such that the first image and the second image are acquired at a rate half of the given rate, and the video image is generated at half the given rate.

8. The method of claim 7, wherein the given rate is at least 60 Hz.

9. The method of claim 6, further comprising: determining the in-focus portion of the first image using one or more contrast analysis algorithms.

10. The method of claim 6, wherein the system further comprises a tracking device configured to be tracked by a navigation system.

11. A non-transitory computer-readable medium storing a computer program, wherein execution of the computer program is for:
at a system comprising: a camera device having a field of view and configured to change between at least two numerical apertures, the camera device comprising: a plate including a first aperture, defining a first numerical aperture, and a second aperture, defining a second numerical aperture, a diameter of the first aperture being larger than a respective diameter of the second aperture; and an actuator configured to automatically move the plate relative to the field of view of the camera device such that a first image is automatically acquired using the first aperture and a second image is automatically acquired using the second aperture, the field of view being a common field of view for both the first image acquired using the first numerical aperture and the second image acquired using the second numerical aperture, the first image comprising: an in-focus portion; and an out-of-focus portion, and the first image being of a higher resolution than the second image, the second image comprising: a first portion corresponding to the in-focus portion of the first image; and a second portion corresponding to the out-of-focus portion of the first image, the second portion being in focus, the first portion and the second portion of the second image comprising same respective features as the in-focus portion and the out-of-focus portion of the first image in the common field of view; an image processing unit; and a display device in communication with the image processing unit,
acquiring, using the camera device, the first image of the field of view at the first numerical aperture;
acquiring, using the camera device, the second image of the field of view at the second numerical aperture smaller than the first numerical aperture;
combining, using the image processing unit, the first image with the second image into a single image by:
extracting the in-focus portion of the first image; and
replacing the first portion of the second image with the in-focus portion of the first image; and,
rendering, at the display device, the single image, the single image being a video image.

* * * * *